US008263603B2

(12) United States Patent
Boebel et al.

(10) Patent No.: US 8,263,603 B2
(45) Date of Patent: Sep. 11, 2012

(54) N3-SUBSTITUTED-N1-SULFONYL-5-FLUOROPYRIMIDINONE DERIVATIVES

(75) Inventors: Timothy A. Boebel, Indianapolis, IN (US); Beth Lorsbach, Indianapolis, IN (US); Timothy P. Martin, Noblesville, IN (US); W. John Owen, Carmel, IN (US); Michael T. Sullenberger, Westfield, IN (US); Jeffery D. Webster, New Palestine, IN (US); Chenglin Yao, Westfield, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/090,616

(22) Filed: Apr. 20, 2011

(65) Prior Publication Data

US 2011/0263627 A1 Oct. 27, 2011

Related U.S. Application Data

(60) Provisional application No. 61/327,855, filed on Apr. 26, 2010.

(51) Int. Cl.
*A61K 31/505* (2006.01)
(52) U.S. Cl. ......................................... 514/274; 544/317
(58) Field of Classification Search .................. 544/317
See application file for complete search history.

(56) References Cited

U.S. PATENT DOCUMENTS

| | | | |
|---|---|---|---|
| 2009/0203647 A1* | 8/2009 | Benko et al. ................... 514/86 |
| 2010/0022538 A1* | 1/2010 | Boebel et al. .............. 514/235.8 |
| 2010/0029482 A1* | 2/2010 | Benko et al. .................. 504/136 |
| 2011/0034493 A1* | 2/2011 | Boebel et al. ................. 514/274 |
| 2011/0053891 A1* | 3/2011 | Boebel et al. ................... 514/63 |

\* cited by examiner

*Primary Examiner* — James O Wilson
*Assistant Examiner* — Alexander R Pagano
(74) *Attorney, Agent, or Firm* — Charles W. Arnett

(57) ABSTRACT

This present disclosure is related to the field of N3-substituted-N1-sulfonyl-5-fluoropyrimidinones and their derivatives and to the use of these compounds as fungicides.

4 Claims, No Drawings

N3-SUBSTITUTED-N1-SULFONYL-5-FLUOROPYRIMIDINONE DERIVATIVES

CROSS-REFERENCE TO RELATED APPLICATIONS

This application claims the benefit of U.S. Provisional Patent Application Ser. No. 61/327,855 filed Apr. 26, 2010, which is expressly incorporated by reference herein.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to N3-substituted-M-sulfonyl-5-fluoropyrimidinone compounds and their use as fungicides. The compounds of the present disclosure may offer protection against ascomycetes, basidiomycetes, deuteromycetes and oomycetes.

One embodiment of the present disclosure may include compounds of Formula I:

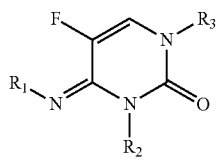

wherein $R_1$ is:
  H;
$R_2$ is:
  $C_1$-$C_6$ alkyl optionally substituted with $R_4$;
  benzyl optionally substituted with 1-3 $R_5$
$R_3$ is —S(O)$_2$$R_6$;
$R_4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, or $C_3$-$C_6$ trialkylsilyl;
$R_5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl, nitro, hydroxyl, or cyano;
$R_6$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl may be optionally substituted with 1-3 $R_5$, or a 5- or 6-membered saturated or unsaturated ring containing 1-3 heteroatoms wherein each ring may be optionally substituted with 1-3 $R_5$.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

As used throughout this specification, the term 'R' refers to the group consisting of $C_{2-8}$ alkyl unless stated otherwise.

The term "alkoxy" refers to an —OR substituent.
The term "alkoxycarbonyl" refers to a —C(O)—OR substituent.
The term "alkylcarbonyl" refers to a —C(O)—R substituent.
The term "alkylthio" refers to an —S—R substituent.
The term "haloalkylthio" refers to an alkylthio, which is substituted with Cl, F, I, or Br or any combination thereof.
The term "trialkylsilyl" refers to —SiR$_3$.
The term "cyano" refers to a —C≡N substituent.
The term "hydroxyl" refers to an —OH substituent.
The term "amino" refers to a —NH$_2$ substituent.
The term "alkylamino" refers to a —N(H)—R substituent.
The term "dialkylamino" refers to a —NR$_2$ substituent.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —NO$_2$ substituent.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, roots, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION OF THE PRESENT DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendable, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 1 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol($C_{12}$-$C_{16}$)ethoxylate; di-sec-butylphenol EO—PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamid, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungicidal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora beticola*), peanuts (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

EXAMPLES

Example 1

Preparation of 1-Benzenesulfonyl-5-fluoro-4-imino-3-methyl-3,4-dihydro-1H-pyrimidin-2-one (Compound 1)

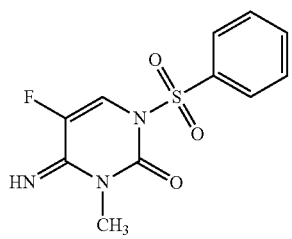

4-Amino-1-benzenesulfonyl-5-fluoro-1H-pyrimidine-2-one (200 mg, 0.74 mmol) was stirred at room temperature in dimethyl formamide (3 mL) together with anhydrous potassium carbonate (210 mg, 1.5 mmol). Iodomethane (210 mg, 1.5 mmol) was added and the mixture was heated at 60° C. for 3 hours. After cooling to room temperature, the mixture was partitioned between ethyl acetate (EtOAc) and water. The organic phase was dried over magnesium sulfate, filtered, and evaporated. The crude product was purified by chromatography on silica gel (gradient, 20 to 80% EtOAc in petroleum ether) to isolate 1-benzenesulfonyl-5-fluoro-4-imino-3-methyl-3,4-dihydro-1H-pyrimidin-2-one (106 mg, 50%) as a white solid: mp 144° C.; $^1$H NMR (600 MHz, DMSO-d$_6$) δ 8.52 (s, 1H), 8.03-8.00 (m, 2H), 7.97 (d, J=5.9 Hz, 1H), 7.80-7.76 (m, 1H), 7.67-7.63 (m, 2H), 3.09 (s, 3H); ESIMS m/z 284 ([M+H]$^+$).

Compounds 2-4 in Table 1 were prepared via this route.

Example 2

Preparation of 1-benzenesulfonyl-5-fluoro-4-imino-3-ethyl-3,4-dihydro-1H-pyrimidin-2-one (Compound 6)

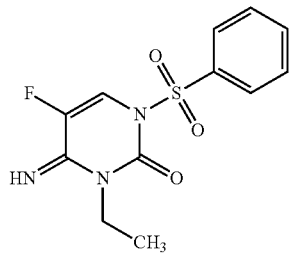

To a 25 mL sealed tube were added 4-amino-1-benzenesulfonyl-5-fluoro-1H-pyrimidine-2-one (1.0 g, 3.71 mmol), anhydrous potassium carbonate (K$_2$CO$_3$; 2.05 g, 14.9 mmol), and N,N-dimethylformamide (DMF; 10 mL), followed by iodoethane (EtI; 3.45 g, 22.3 mmol). The reaction vessel was sealed, and the reaction mixture was warmed to 60° C. and stirred for 1 hour. The reaction mixture was cooled to room temperature, diluted with ethyl acetate (EtOAc; 250 mL), and washed with water (H$_2$O; 3×100 mL). The organic phase was dried over magnesium sulfate (MgSO$_4$), filtered, and the solvent evaporated under reduced pressure. Purification by flash chromatography (SiO$_2$, EtOAc/Hexanes gradient) afforded benzenesulfonyl-5-fluoro-4-imino-3-ethyl-3,4-dihydro-1H-pyrimidin-2-one as a pale yellow solid (200 mg; 18%): mp 163-166° C.; $^1$H NMR (400 MHz, DMSO-d$_6$) δ 8.82 (m, 1H), 8.29 (d, J=6.8 Hz, 1H), 8.02 (dd, J=8.4, 1.1 Hz, 2H), 7.79 (ddd, J=6.9, 2.3, 1.1 Hz, 1H), 7.66 (dd, J=10.7, 4.9 Hz, 2H), 3.31 (q, J=7.2 Hz, 2H), 1.09 (t, J=7.2 Hz, 3H); ESIMS m/z 298 ([M+H]$^+$).

Compounds 7-9 were prepared as described in Example 2.

Example 3

Preparation of 3-benzyl-5-fluoro-4-imino-1-(4-methoxyphenylsulfonyl)-3,4-dihydropyrimidin-2(1H)-one (Compound 5)

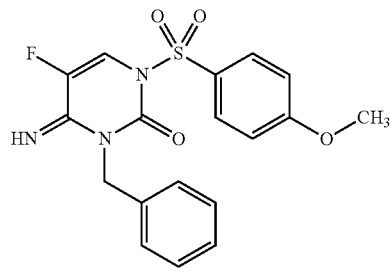

In a 20 mL microwave vial, 5-fluoro-4-imino-1-(4-methoxyphenylsulfonyl)-3,4-dihydropyrimidin-2(1H)-one (111 mg, 0.37 mmol) was stirred at room temperature in dimethyl formamide (3 mL) together with anhydrous potassium carbonate (210 mg, 0.55 mmol). Benzylbromide (89 μL, 0.75 mmol) was added. The reaction was capped and placed on a Biotage Initiator microwave reactor for 20 min at 130° C., with external IR-sensor temperature monitoring from the side of the vessel. The reaction mixture was cooled to room temperature, diluted with ethyl acetate (EtOAc; 250 mL), and washed with water (H₂O; 3×100 mL). The organic phase was dried over magnesium sulfate (MgSO₄), filtered, and the solvent evaporated under reduced pressure. Purification by flash chromatography (SiO₂, EtOAc/Hexanes gradient) afforded 3-benzyl-5-fluoro-4-imino-1-(4-methoxyphenylsulfonyl)-3,4-dihydropyrimidin-2(1H)-one as a pale yellow oil (15 mg; 11%): $^1$H NMR (400 MHz, CDCl₃) δ 8.09-8.02 (m, 3H), 7.38-7.27 (m, 6H), 7.00-6.96 (m, 2H), 4.65 (d, J=5.7 Hz, 2H), 3.87 (s, 3H). ESIMS m/z 391 ([M+H]$^+$).

TABLE I

Compounds and Related Characterization Data

| Compound No. | Structure | Appearance | mp (° C.) | ESIMS + | $^1$H NMR $^1$ |
|---|---|---|---|---|---|
| 1 | 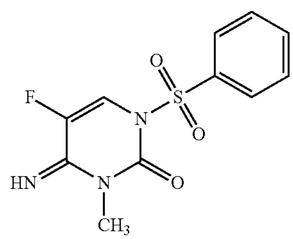 | white solid | 144 | 284 | δ 8.52 (s, 1H), 8.03-8.00 (m, 2H), 7.97 (d, J = 5.9 Hz, 1H), 7.80-7.76 (m, 1H), 7.67-7.63 (m, 2H), 3.09 (s, 3H). |
| 2 | 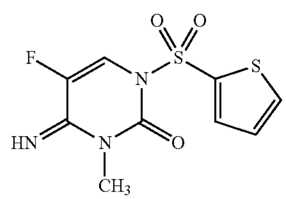 | pale yellow solid | 136-139 | 290 | δ 8.00 (d, J = 1.32 Hz, 1H), 7.81 (m, 2H), 7.69 (d, J = 5.27 Hz, 1H), 7.18 (m, 1H), 3.37 (s, 3H). |
| 3 | 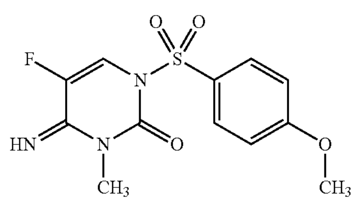 | pale yellow solid | 158-162 | 314 | δ 8.01 (d, J = 9.22 Hz, 2H), 7.74 (d, J = 5.27 Hz, 1H), 7.04 (d, J = 9.23 Hz, 2H), 3.90 (s, 3H), 3.31 (s, 3H). |
| 4 | 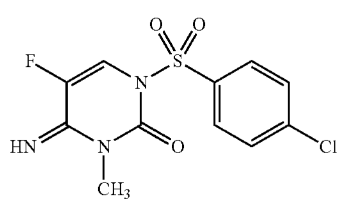 | white solid | 147-150 | 318, 321 | δ 8.02 (d, J = 8.9 Hz, 2H), 7.71 (d, J = 5.27 Hz, 1H), 7.57 (d, J = 8.90 Hz, 2H), 3.32 (s, 3H). |
| 5 | 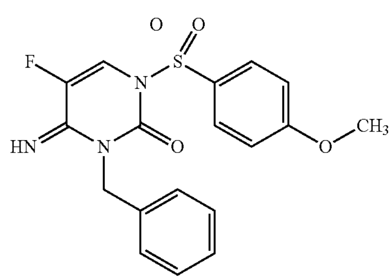 | Yellow Oil | — | 391 | $^1$H NMR (400 MHz, CDCl₃) δ 8.09-8.02 (m, 3H), 7.38-7.27 (m, 6H), 7.00-6.96 (m, 2H), 4.65 (d, J = 5.7 Hz, 2H), 3.87 (s, 3H). |

TABLE I-continued

Compounds and Related Characterization Data

| Compound No. | Structure | Appearance | mp (° C.) | ESIMS + | ¹H NMR[1] |
|---|---|---|---|---|---|
| 6 | (structure) | Pale Yellow solid | 163-166 | 298 | δ 8.82 (m, 1H), 8.29 (d, J = 6.8 Hz, 1H), 8.02 (dd, J = 8.4, 1.1 Hz, 2H), 7.79 (ddd, J = 6.9, 2.3, 1.1 Hz, 1H), 7.66 (dd, J = 10.7, 4.9 Hz, 2H), 3.31 (q, J = 7.2 Hz, 2H), 1.09 (t, J = 7.2 Hz, 3H). |
| 7 | (structure) | Pale Yellow Solid | 165-168 | 332 | ¹H NMR (400 MHz, DMSO-d6 + D₂O (95:5)) δ 8.26 (d, J = 6.7 Hz, 1H), 8.04 (d, J = 8.8 Hz, 2H), 7.75 (d, J = 8.8 Hz, 2H), 3.33 (q, J = 7.3 Hz, 2H), 1.09 (t, J = 7.2 Hz, 3H). |
| 8 | (structure) | Pale Yellow Solid | 107-111 | 328 | δ 8.75 (dd, J = 7.2, 3.4 Hz, 1H), 8.26 (d, J = 6.8 Hz, 1H), 7.96 (d, J = 8.9 Hz, 2H), 7.17 (d, J = 9.0 Hz, 2H), 3.87 (s, 3H), 3.32 (q, J = 7.2 Hz, 2H), 1.09 (t, J = 7.2 Hz, 3H). |
| 9 | (structure) | Pale Yellow Solid | 182-185 | 366 | ¹H NMR (400 MHz, DMSO-d6 + D₂O (95:5)) δ 8.29 (d, J = 6.5 Hz, 1H), 7.71 (m, 3H), 3.35 (q, J = 7.2 Hz, 2H), 1.11 (t, J = 1.2 Hz, 3H). |

[1] All spectra were recorded in DMSO-d6 at 300, 400 or 600 MHz unless otherwise stated.

Example 4

Evaluation of Fungicidal Activity: Leaf Blotch of Wheat (*Mycosphaerella graminicola*; anamorph: *Septoria tritici*; Bayer code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two days in a lighted dew chamber) to permit spores to germinate and infect the leaf. The plants were then transferred to a greenhouse for disease to develop.

The following table presents the activity of typical compounds of the present disclosure when evaluated in these experiments. The effectiveness of the test compounds in controlling disease was determined by assessing the severity of disease on treated plants, and then converting the severity to percent control based on the level of disease on untreated, inoculated plants.

In each case of Table II the rating scale is as follows:

| % Disease Control | Rating |
|---|---|
| 76-100 | A |
| 51-75 | B |
| 26-50 | C |
| 0-25 | D |
| Not Tested | E |

TABLE II

One-Day Protectant (1 DP) and Three-Day Curative
(3 DC) Activity of Compounds on SEPTTR at 100 ppm

| Cmpd | SEPTTR 100 PPM 1 DP | SEPTTR 100 PPM 3 DC |
|---|---|---|
| 1 | A | A |
| 2 | A | A |
| 3 | A | A |
| 4 | A | A |
| 5 | D | D |
| 6 | D | D |
| 7 | B | A |
| 8 | D | B |
| 9 | D | A |

What is claimed is:

1.

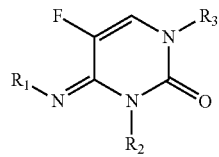

wherein $R_1$ is:
 H
$R_2$ is:
 $C_1$-$C_6$ alkyl optionally substituted with $R_4$;
 benzyl optionally substituted with 1-3 $R_5$
$R_3$ is —$S(O)_2R_6$;
$R_4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, $C_2$-$C_6$ alkylaminocarbonyl, hydroxyl, or $C_3$-$C_6$ trialkylsilyl;
$R_5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl, nitro, hydroxyl, or cyano;
$R_6$ is $C_1$-$C_6$ alkyl, $C_1$-$C_6$ haloalkyl, amino, $C_1$-$C_6$ alkylamino, $C_2$-$C_6$ dialkylamino, a phenyl or benzyl wherein each of the phenyl or the benzyl may be optionally substituted with 1-3 $R_5$, or a 5- or 6-membered saturated or unsaturated ring containing 1-3 heteroatoms wherein each ring may be optionally substituted with 1-3 $R_5$.

2. A composition for the control of a fungal pathogen including the compound of claim 1 and a phytologically acceptable carrier material.

3. The composition of claim 2 wherein the fungal pathogen is Apple Scab (*Venturia inaequalis*), Leaf Blotch of Wheat (*Septoria tritici*), Leaf spot of sugarbeets (*Cercospora beticola*), Leaf Spot of peanut (*Cercospora arachidicola*), and Black Sigatoka (*Mycosphaerella fijiensis*).

4. A method for the control and prevention of fungal attack on a plant, the method including the steps of:
applying a fungicidally effective amount of at least one of the compounds of claim 1 to at least one of the plant, an area adjacent to the plant, soil adapted to support growth of the plant, a root of the plant, foliage of the plant, and a seed adapted to produce the plant.

* * * * *